United States Patent
Moffitt et al.

(10) Patent No.: US 9,283,375 B2
(45) Date of Patent: Mar. 15, 2016

(54) LEADS WITH SEGMENTED ELECTRODES FOR ELECTRICAL STIMULATION OF PLANAR REGIONS AND METHODS OF MAKING AND USING

(71) Applicant: BOSTON SCIENTIFIC NEUROMODULATION CORPORATION, Valencia, CA (US)

(72) Inventors: Michael Adam Moffitt, Valencia, CA (US); Anne Margaret Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/517,746

(22) Filed: Oct. 17, 2014

(65) Prior Publication Data
US 2015/0038979 A1    Feb. 5, 2015

Related U.S. Application Data

(63) Continuation of application No. 13/368,733, filed on Feb. 8, 2012, now abandoned.

(60) Provisional application No. 61/440,546, filed on Feb. 8, 2011.

(51) Int. Cl.
*A61N 1/00* (2006.01)
*A61N 1/05* (2006.01)

(52) U.S. Cl.
CPC ................................ *A61N 1/0534* (2013.01)

(58) Field of Classification Search
CPC .............................................. A61N 1/04–1/06
See application file for complete search history.

(56) References Cited

U.S. PATENT DOCUMENTS

| | | |
|---|---|---|
| 4,602,624 A | 7/1986 | Naples et al. |
| 4,630,611 A | 12/1986 | King |
| 4,744,370 A | 5/1988 | Harris |
| 5,000,194 A | 3/1991 | van den Honert et al. |
| 5,135,001 A | 8/1992 | Sinofsky et al. |

(Continued)

FOREIGN PATENT DOCUMENTS

| | | |
|---|---|---|
| EP | 0580928 A1 | 2/1994 |
| EP | 0650694 B1 | 7/1998 |

(Continued)

OTHER PUBLICATIONS

U.S. Appl. No. 14/286,889, filed May 23, 2014.

(Continued)

*Primary Examiner* — Scott Getzow
(74) *Attorney, Agent, or Firm* — Lowe Graham Jones PLLC; Bruce E. Black

(57) ABSTRACT

One embodiment is a stimulation lead that includes a lead body having a longitudinal surface, a distal end, and a proximal end; and multiple electrodes disposed along the longitudinal surface of the lead body near the distal end of the lead body. The electrodes include multiple groups of segmented electrodes with each group of segmented electrodes having multiple segmented electrodes disposed at a same longitudinal position along the lead. For at least one first group of segmented electrodes, a first pair of the segmented electrodes in the first group are disposed on opposite sides of the lead body and are electrically ganged together by a conductor therebetween.

20 Claims, 5 Drawing Sheets

(56) References Cited

U.S. PATENT DOCUMENTS

| | | |
|---|---|---|
| 5,374,285 A | 12/1994 | Vaiani et al. |
| 5,458,629 A | 10/1995 | Baudino et al. |
| 5,522,874 A | 6/1996 | Gates |
| 5,711,316 A | 1/1998 | Elsberry et al. |
| 5,713,922 A | 2/1998 | King |
| 5,800,350 A | 9/1998 | Coppleson et al. |
| 5,843,148 A | 12/1998 | Gijsbers et al. |
| 5,938,688 A | 8/1999 | Schiff |
| 5,957,966 A * | 9/1999 | Schroeppel et al. .......... 607/122 |
| 5,987,361 A | 11/1999 | Mortimer |
| 6,018,684 A | 1/2000 | Bartig et al. |
| 6,134,478 A | 10/2000 | Spehr |
| 6,161,047 A | 12/2000 | King et al. |
| 6,167,311 A | 12/2000 | Rezai |
| 6,322,559 B1 | 11/2001 | Daulton et al. |
| 6,510,347 B2 | 1/2003 | Borkan |
| 6,556,873 B1 * | 4/2003 | Smits ........................... 607/122 |
| 6,564,078 B1 | 5/2003 | Marino et al. |
| 6,678,564 B2 | 1/2004 | Ketterl et al. |
| 6,757,970 B1 | 7/2004 | Kuzma et al. |
| 7,027,852 B2 | 4/2006 | Helland |
| 7,047,084 B2 | 5/2006 | Erickson et al. |
| 7,203,548 B2 | 4/2007 | Whitehurst et al. |
| 7,292,890 B2 | 11/2007 | Whitehurst et al. |
| 7,489,971 B1 | 2/2009 | Franz |
| 7,668,601 B2 | 2/2010 | Hegland et al. |
| 7,761,985 B2 | 7/2010 | Hegland et al. |
| 7,809,446 B2 | 10/2010 | Meadows |
| 7,822,482 B2 | 10/2010 | Gerber |
| 7,840,188 B2 | 11/2010 | Kurokawa |
| 7,848,802 B2 | 12/2010 | Goetz |
| 7,856,707 B2 | 12/2010 | Cole |
| 7,860,570 B2 | 12/2010 | Whitehurst et al. |
| 7,974,705 B2 | 7/2011 | Zdeblick et al. |
| 7,979,140 B2 | 7/2011 | Schulman |
| 8,000,808 B2 | 8/2011 | Hegland et al. |
| 8,019,440 B2 | 9/2011 | Kokones et al. |
| 8,036,755 B2 | 10/2011 | Franz |
| 8,041,309 B2 | 10/2011 | Kurokawa |
| 8,099,177 B2 | 1/2012 | Dahlberg |
| 8,225,504 B2 | 7/2012 | Dye et al. |
| 8,295,944 B2 | 10/2012 | Howard et al. |
| 8,321,025 B2 | 11/2012 | Bedenbaugh |
| 8,359,107 B2 | 1/2013 | Pianca et al. |
| 8,391,985 B2 | 3/2013 | McDonald |
| 8,583,237 B2 | 11/2013 | Bedenbaugh |
| 8,688,235 B1 | 4/2014 | Pianca et al. |
| 2001/0023368 A1 | 9/2001 | Black et al. |
| 2002/0156513 A1 | 10/2002 | Borkan |
| 2002/0183817 A1 | 12/2002 | Van Venrooij et al. |
| 2004/0215301 A1 * | 10/2004 | Lokhoff et al. ................ 607/116 |
| 2005/0015130 A1 | 1/2005 | Gill |
| 2005/0038489 A1 | 2/2005 | Grill |
| 2005/0171587 A1 | 8/2005 | Daglow et al. |
| 2006/0025841 A1 | 2/2006 | McIntyre |
| 2006/0247697 A1 | 11/2006 | Sharma et al. |
| 2007/0112403 A1 | 5/2007 | Moffitt et al. |
| 2007/0150036 A1 | 6/2007 | Anderson |
| 2007/0168007 A1 | 7/2007 | Kuzma et al. |
| 2007/0203546 A1 | 8/2007 | Stone et al. |
| 2007/0219551 A1 | 9/2007 | Honour et al. |
| 2008/0077186 A1 | 3/2008 | Thompson et al. |
| 2008/0103580 A1 | 5/2008 | Gerber |
| 2008/0114230 A1 | 5/2008 | Addis |
| 2008/0215125 A1 | 9/2008 | Farah et al. |
| 2008/0255647 A1 | 10/2008 | Jensen et al. |
| 2009/0187222 A1 | 7/2009 | Barker |
| 2009/0204192 A1 | 8/2009 | Carlton et al. |
| 2009/0204193 A1 | 8/2009 | Kokones et al. |
| 2009/0276021 A1 | 11/2009 | Meadows et al. |
| 2010/0030298 A1 | 2/2010 | Martens et al. |
| 2010/0036468 A1 | 2/2010 | Decre et al. |
| 2010/0076535 A1 | 3/2010 | Pianca et al. |
| 2010/0077606 A1 | 4/2010 | Black et al. |
| 2010/0082076 A1 | 4/2010 | Lee et al. |
| 2010/0094387 A1 | 4/2010 | Pianca et al. |
| 2010/0100152 A1 | 4/2010 | Martens et al. |
| 2010/0268298 A1 | 10/2010 | Moffitt et al. |
| 2010/0269338 A1 | 10/2010 | Dye |
| 2010/0269339 A1 | 10/2010 | Dye et al. |
| 2010/0287770 A1 | 11/2010 | Dadd et al. |
| 2011/0005069 A1 | 1/2011 | Pianca |
| 2011/0047795 A1 | 3/2011 | Turner et al. |
| 2011/0056076 A1 | 3/2011 | Hegland et al. |
| 2011/0077699 A1 | 3/2011 | Swanson et al. |
| 2011/0078900 A1 | 4/2011 | Pianca et al. |
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0131808 A1 | 6/2011 | Gill |
| 2011/0238129 A1 | 9/2011 | Moffitt et al. |
| 2011/0245903 A1 | 10/2011 | Schulte et al. |
| 2011/0301665 A1 | 12/2011 | Mercanzini et al. |
| 2011/0313500 A1 | 12/2011 | Barker et al. |
| 2012/0016378 A1 | 1/2012 | Pianca et al. |
| 2012/0046710 A1 | 2/2012 | DiGiore et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2013/0109254 A1 | 5/2013 | Klardie et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0317587 A1 | 11/2013 | Barker |
| 2013/0325091 A1 | 12/2013 | Pianca et al. |
| 2014/0039587 A1 | 2/2014 | Romero |
| 2014/0039590 A1 | 2/2014 | DiGiore et al. |
| 2014/0142671 A1 | 5/2014 | Moffitt et at |
| 2014/0180375 A1 | 6/2014 | Pianca et al. |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 0038574 A1 | 7/2000 |
| WO | 0158520 A1 | 8/2001 |
| WO | 02068042 A1 | 9/2002 |
| WO | 2004045707 A1 | 6/2004 |
| WO | 2008018067 A2 | 2/2008 |
| WO | 2008053789 A1 | 5/2008 |
| WO | 2008/100841 A1 | 8/2008 |
| WO | 2009025816 A1 | 2/2009 |
| WO | 2009102536 A1 | 8/2009 |
| WO | 2013162775 A2 | 10/2013 |
| WO | 2014018092 A1 | 1/2014 |

OTHER PUBLICATIONS

U.S. Appl. No. 14/286,934, filed May 23, 2014.
U.S. Appl. No. 14/286,829, filed May 23, 2014.
U.S. Appl. No. 14/286,940, filed May 23, 2014.
U.S. Appl. No. 14/332,212, filed Jul. 15, 2014.
U.S. Appl. No. 14/452,461, filed Aug. 5, 2014.
U.S. Appl. No. 14/286,797, filed May 23, 2014.
U.S. Appl. No. 14/469,214, filed Aug. 26, 2014.
Official Communication for U.S. Appl. No. 13/368,733 mailed Jul. 17, 2014.
Official Communication for U.S. Appl. No. 13/368,733 mailed Sep. 5, 2013.
Official Communication for U.S. Appl. No. 13/368,733 mailed Apr. 26, 2013.
U.S. Appl. No. 14/325,249, filed Jul. 7, 2014.
U.S. Appl. No. 14/557,211, filed Dec. 1, 2014.

* cited by examiner

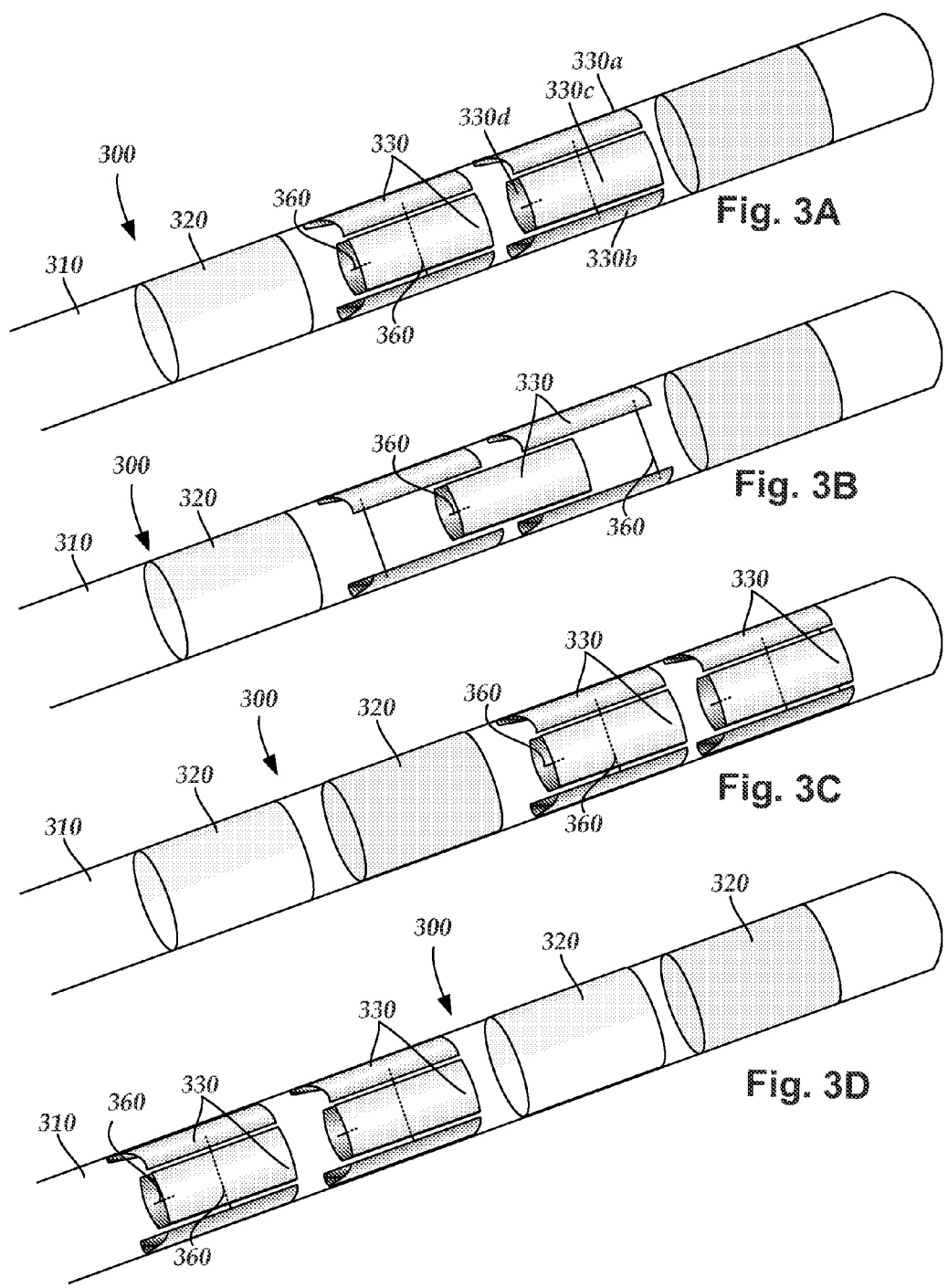

LEADS WITH SEGMENTED ELECTRODES FOR ELECTRICAL STIMULATION OF PLANAR REGIONS AND METHODS OF MAKING AND USING

CROSS-REFERENCE TO RELATED APPLICATIONS

This application is a continuation of U.S. patent application Ser. No. 13/368,733 filed Feb. 8, 2012 which claims the benefit under 35 U.S.C. §119(e) of U.S. Provisional Patent Application Ser. No. 61/440,546 filed on Feb. 8, 2011, both of which are incorporated herein by reference.

FIELD

The invention is directed to the area of electrical stimulation systems and methods of making and using the systems. The present invention is also directed to electrical stimulation leads with segmented electrodes that can be used for electrical stimulation of planar regions, as well as methods of making and using the segmented electrodes, leads, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a stimulation lead that includes a lead body having a longitudinal surface, a distal end, and a proximal end; and multiple electrodes disposed along the longitudinal surface of the lead body near the distal end of the lead body. The electrodes include multiple groups of segmented electrodes with each group of segmented electrodes having multiple segmented electrodes disposed at a same longitudinal position along the lead. For at least one first group of segmented electrodes, a first pair of the segmented electrodes in the first group are disposed on opposite sides of the lead body and are electrically ganged together by a conductor therebetween.

Another embodiment is a kit for implanting a stimulation lead into a patient. The kit includes a stimulation lead having a longitudinal surface, a distal end, and at least one electrode disposed along the longitudinal surface of the stimulation lead near the distal end of the stimulation lead. A portion of the stimulation lead upon which the electrode(s) are disposed has a non-circular cross-sectional shape. The kit also includes at least one microelectrode lead having a distal end and at least one microelectrode disposed at the distal end of the microelectrode lead. The kit further includes an introducer defining a lumen configured and arranged to receive the stimulation lead. The introducer has at least one interior wall extending into the lumen and defining at least one microelectrode lumen that is configured and arranged to receive, and hold within the microelectrode lumen, one of the at least one microelectrode leads.

A further embodiment is a method for stimulating tissue that includes implanting a lead comprising a longitudinal surface, a distal end, a proximal end, two main portions disposed at the distal end of the lead, a bendable portion disposed between the two main portions, multiple electrodes disposed on surfaces of the two main portions of the lead, and multiple terminals disposed along the proximal end of the lead and electrically coupled to the electrodes. The bendable portion is bent so that the two main portions are disposed opposite each other and each electrode has an exposed surface through which electrical energy can be supplied to stimulate adjacent tissue when the stimulation lead is implanted. The method further includes retaining the lead in the patient with the bendable portion bent; and stimulating adjacent tissue using at least one of the electrodes.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 3A is a perspective view of an embodiment of a portion of a lead having a plurality of segmented electrodes with selected electrodes electrically ganged, according to the invention;

FIG. 3B is a perspective view of a second embodiment of a portion of a lead having a plurality of segmented electrodes with selected electrodes electrically ganged, according to the invention;

FIG. 3C is a perspective view of a third embodiment of a portion of a lead having a plurality of segmented electrodes with selected electrodes electrically ganged, according to the invention;

FIG. 3D is a perspective view of a fourth embodiment of a portion of a lead having a plurality of segmented electrodes with selected electrodes electrically ganged, according to the invention;

DETAILED DESCRIPTION

Figure 1:
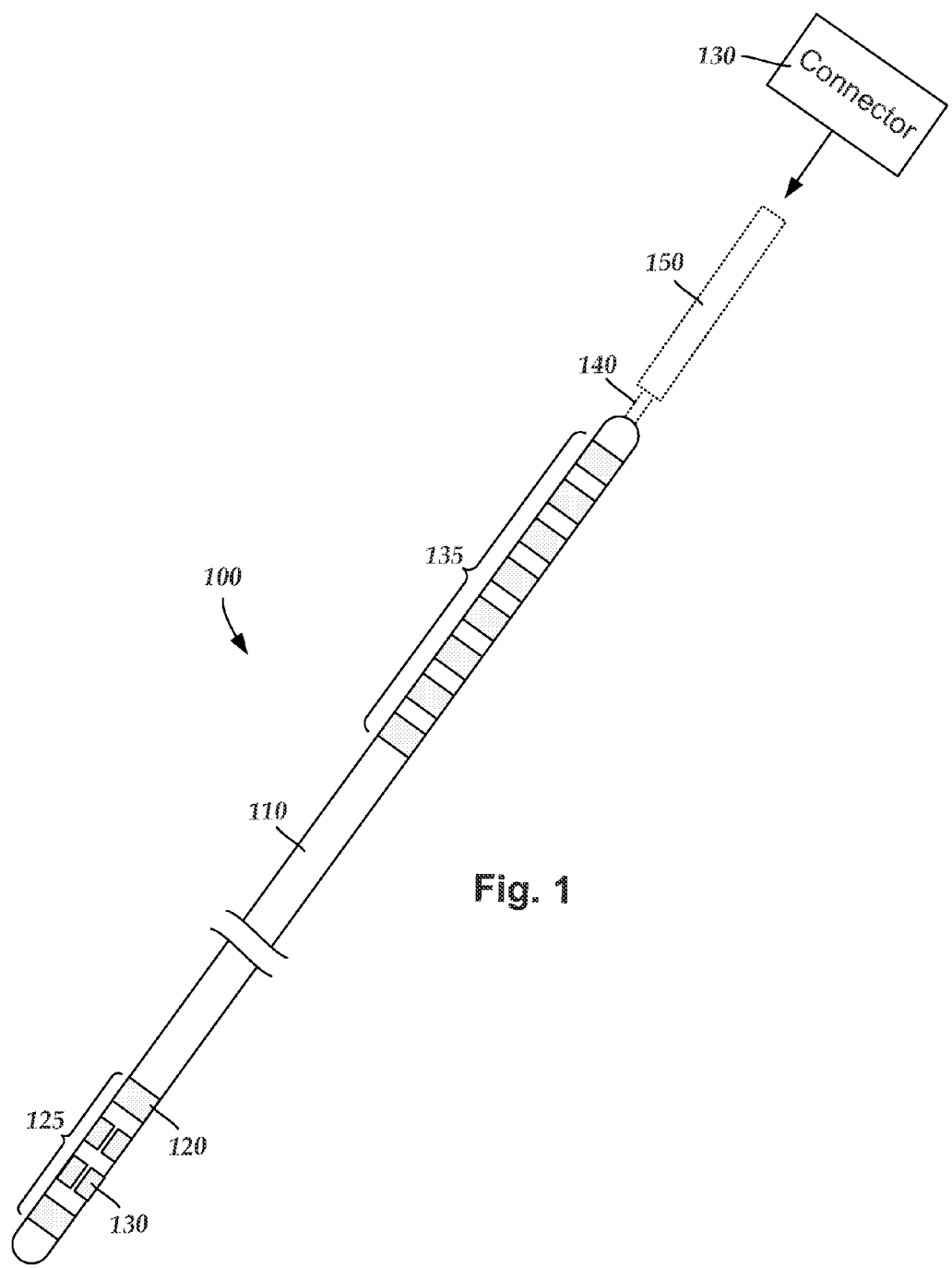
FIG. 1 is a schematic side view of one embodiment of a device for brain stimulation, according to the invention.

The invention is directed to the area of electrical stimulation systems and methods of making and using the systems. The present invention is also directed to electrical stimulation leads with segmented electrodes that can be used for electrical stimulation of planar regions, as well as methods of making and using the segmented electrodes, leads, and electrical stimulation systems.

A lead for deep brain stimulation may include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position.

A practitioner may determine the position of the target neurons using the recording electrode(s) and then position the stimulation electrode(s) accordingly without removal of a recording lead and insertion of a stimulation lead. In some embodiments, the same electrodes can be used for both recording and stimulation. In some embodiments, separate leads can be used; one with recording electrodes which identify target neurons, and a second lead with stimulation electrodes that replaces the first after target neuron identification. A lead may include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes. For illustrative purposes, the leads are described herein relative to use for deep brain stimulation, but it will be understood that any of the leads can be used for applications other than deep brain stimulation, including spinal cord stimulation and stimulation of other nerves and tissues.

Deep brain stimulation devices and leads are described in, for example, U.S. Pat. No. 7,809,446 ("Devices and Methods For Brain Stimulation"), U.S. Patent Application Publication No. 2010/0076535 A1 ("Leads With Non-Circular-Shaped Distal Ends For Brain Stimulation Systems and Methods of Making and Using"), U.S. Patent Application Publication 2007/0150036 A1 ("Stimulator Leads and Methods For Lead Fabrication"), U.S. patent application Ser. No. 12/177,823 ("Lead With Transition and Methods of Manufacture and Use"), U.S. Patent Application Publication No. 2009/0276021 A1 ("Electrodes For Stimulation Leads and Methods of Manufacture and Use"), U.S. Patent Application Ser. No. 61/170,037 ("Deep Brain Stimulation Current Steering with Split Electrodes"), U.S. Patent Application Ser. No. 61/022,953, U.S. Patent Application Ser. No. 61/316,759, U.S. Patent Application Publication No. 2009/0187222 A1, and U.S. Patent Application Ser. No. 61/426,784. Each of these references is incorporated herein by reference.

FIG. 1 illustrates one embodiment of a device 100 for brain stimulation. The device includes a lead 110, a plurality of electrodes 125 disposed at least partially about a circumference of the lead 110, a plurality of terminals 135, a connector 130 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 130 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator may have more or fewer than eight stimulation channels (e.g., 4-, 6-, 16-, 32-, or more stimulation channels). The control unit may have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more of the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 110. Ring electrodes, however, typically do not enable stimulus current to be directed to only one side of the lead. Segmented electrodes, however, can be used to direct stimulus current to one side, or even a portion of one side, of the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

The lead 100 includes a lead body 110, one or more optional ring electrodes 120, and a plurality of sets of segmented electrodes 130. The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 1 to 1.5 mm. In at least some embodiments, the lead 100 has a length of at least 10 cm and the length of the lead 100 may be in the range of 25 to 70 cm.

The electrodes may be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 120 may be disposed on any part of the lead body 110, usually near a distal end of the lead 100. In FIG. 1, the lead 100 includes two ring electrodes 120. Any number of ring electrodes 120 may be disposed along the length of the lead body 110 including, for example, one, two three, four, five, six, seven, eight, nine, ten, eleven, twelve, thirteen, fourteen, fifteen, sixteen or more ring electrodes 120. It will be understood that any number of ring electrodes may be disposed along the length of the lead body 110. In some embodiments, the ring electrodes 120 are substantially cylindrical and wrap around the entire circumference of the lead body 110. In some embodiments, the outer diameters of the ring electrodes 120 are substantially equal to the outer diameter of the lead body 110. The length of the ring electrodes 120 may vary according to the desired treatment and the location of the target neurons. In some embodiments the length of the ring electrodes 120 are less than or equal to the diameters of the ring electrodes 120. In other embodiments, the lengths of the ring electrodes 120 are greater than the diameters of the ring electrodes 120.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue.

In FIG. 1, the lead 100 is shown having a plurality of segmented electrodes 130. Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110.

The segmented electrodes 130 may be grouped into sets of segmented electrodes, where each set is disposed around a circumference of the lead 100 at a particular longitudinal portion of the lead 100. The lead 100 may have any number segmented electrodes 130 in a given set of segmented electrodes. The lead 100 may have one, two, three, four, five, six, seven, eight, or more segmented electrodes 130 in a given set. In at least some embodiments, each set of segmented electrodes 130 of the lead 100 contains the same number of segmented electrodes 130. The segmented electrodes 130 disposed on the lead 100 may include a different number of electrodes than at least one other set of segmented electrodes 130 disposed on the lead 100.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 100) may be identical in size and shape.

Each set of segmented electrodes 130 may be disposed around the circumference of the lead body 110 to form a substantially cylindrical shape around the lead body 110. The spacing between individual electrodes of a given set of the segmented electrodes may be the same, or different from, the spacing between individual electrodes of another set of segmented electrodes on the lead 100. In at least some embodiments, equal spaces, gaps or cutouts are disposed between each segmented electrode 130 around the circumference of the lead body 110. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 110.

Conductor wires that attach to the ring electrodes 120 or segmented electrodes 130 extend along the lead body 110. These conductor wires may extend through the material of the lead 100 or along one or more lumens defined by the lead 100, or both. The conductor wires are presented at a connector (via terminals) for coupling of the electrodes 120, 130 to a control unit (not shown).

When the lead 100 includes both ring electrodes 120 and segmented electrodes 130, the ring electrodes 120 and the segmented electrodes 130 may be arranged in any suitable configuration. For example, when the lead 100 includes two sets of ring electrodes 120 and two sets of segmented electrodes 130, the ring electrodes 120 can flank the two sets of segmented electrodes 130 (see e.g., FIG. 1). Alternately, the two sets of ring electrodes 120 can be disposed proximal to the two sets of segmented electrodes 130 (see e.g., FIG. 3C), or the two sets of ring electrodes 120 can be disposed distal to the two sets of segmented electrodes 130 (see e.g., FIG. 3D). It will be understood that other configurations are possible as well (e.g., alternating ring and segmented electrodes, or the like).

By varying the location of the segmented electrodes 130, different coverage of the target neurons may be selected. For example, the electrode arrangement of FIG. 3C may be useful if the physician anticipates that the neural target will be closer to a distal tip of the lead body 110, while the electrode arrangement of FIG. 3D may be useful if the physician anticipates that the neural target will be closer to a proximal end of the lead body 110.

Any combination of ring electrodes 120 and segmented electrodes 130 may be disposed on the lead 100. For example, the lead may include a first ring electrode 120, two sets of segmented electrodes; each set formed of four segmented electrodes 130, and a final ring electrode 120 at the end of the lead. This configuration may simply be referred to as a 1-4-4-1 configuration. It may be useful to refer to the electrodes with this shorthand notation. Thus, the embodiment of FIG. 3C may be referred to as a 1-1-4-4 configuration, while the embodiment of FIG. 3D may be referred to as a 4-4-1-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 2:
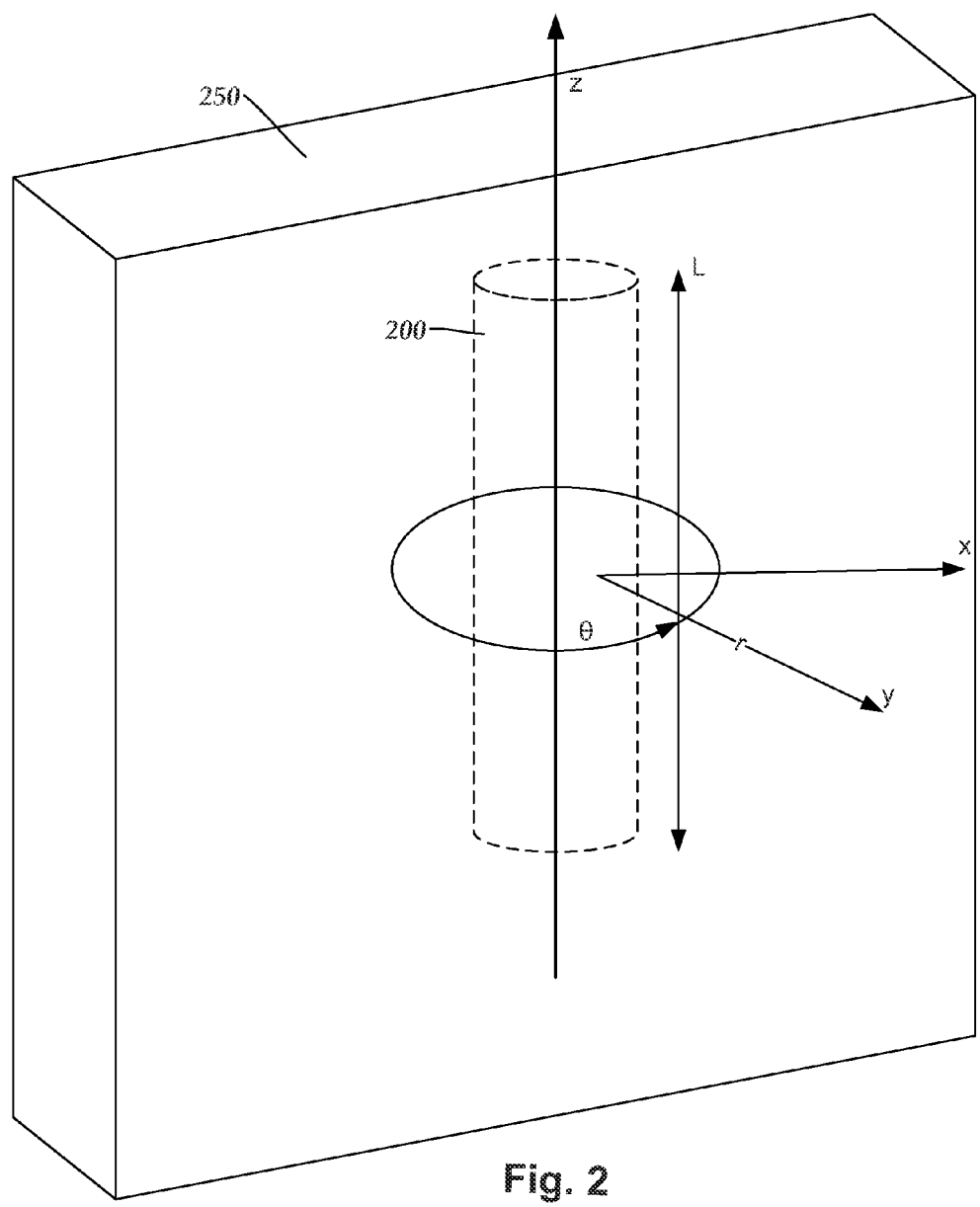
FIG. 2 is a schematic diagram of radial current steering along various electrode levels along the length of a lead, according to the invention.

FIG. 2 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 2, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

Returning to FIG. 1, when the lead 100 includes a plurality of sets of segmented electrodes 130, it may be desirable to form the lead 100 such that corresponding electrodes of different sets of segmented electrodes 130 are radially aligned with one another along the length of the lead 100 (see e.g., the segmented electrodes 130 shown in FIG. 1). Radial alignment between corresponding electrodes of different sets of segmented electrodes 130 along the length of the lead 100 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 100 are radially aligned with one another and do not radially shift in relation to one another during manufacturing of the lead 100.

In other embodiments, individual electrodes in the two sets of segmented electrodes 130 are staggered relative to one another along the length of the lead body 110. In some cases, the staggered positioning of corresponding electrodes of different sets of segmented electrodes along the length of the lead 100 may be designed for a specific application.

Segmented electrodes can be used to tailor the stimulation region so that, instead of stimulating tissue around the circumference of the lead as would be achieved using a ring electrode, the stimulation region can be directionally targeted. In some instances, it is desirable to target a parallelepiped (or slab) region 250 that contains the electrodes of the lead 200, as illustrated in FIG. 2. One arrangement for directing a stimulation field into a parallelepiped region uses segmented electrodes disposed on opposite sides of a lead.

FIGS. 3A-3D illustrate leads 300 with segmented electrodes 330, optional ring electrodes 320, and a lead body 310. The groups of segmented electrodes 330 include either two (FIG. 3B) or four (FIGS. 3A, 3C, and 3D) segmented electrodes. It will be recognized that other groups of segmented electrodes with an even number of electrodes in the group can also be used. In these embodiments, segmented electrodes on opposite sides of the lead are ganged (i.e., electrically coupled) together, as illustrated schematically by the lines 360.

One arrangement for ganging two segmented electrodes together which includes coupling the two electrodes (for example, electrodes 330a and 330b) using a conductor (represented by line 360) that passes through the lead body. This conductor (represented by line 360) can be coupled to another conductor (not shown) that passes through the lead body to the proximal end of the lead to provide for connection to a terminal or contact at the proximal end of the lead. Alternatively, one electrode (for example, electrode 330a) is electrically coupled to a conductor (not shown) that passes through the lead body to the proximal end of the lead to provide for connection to a terminal or contact at the proximal end of the lead and the other electrode (for example, electrode 330b) is coupled to the first electrode by the conductor represented by line 360. This conductor might be a wire or may be a thin, flat conductor.

In operation, stimulation current is applied through the ganged segmented electrodes (for example, electrodes 330a and 330b). For example, the ganged segmented electrodes can operate as cathodes. In some embodiments, other ganged electrodes (for example, electrodes 330c and 330d) may be assigned the opposite polarity (for example, as anodes) which may further direct the stimulation field into the desired parallelepiped region.

As illustrated in FIGS. 3A, 3C, and 3D, multiple pairs of ganged segmented electrodes 330 can be provided in each group of segmented electrodes. The pairs of ganged segmented electrodes 330 are radially offset from each other. For example, two pairs may be radially offset by an angle in the range of 75 to 115 degrees or by an angle in the range of 80 to 110 degrees or be an angle of 90 degrees.

As illustrated in FIG. 3B, the pairs of ganged segmented electrodes can be longitudinally staggered with respect to each other. As illustrated in FIG. 3B, the staggered pairs of ganged segmented electrodes may include electrode portions that are at a same longitudinal position (i.e., the two pairs overlap longitudinally—but not radially). In other embodiments, the electrodes of the staggered pairs do not overlap longitudinally (i.e., no portions of the electrodes of the two pairs have the same longitudinal position on the lead).

Any other suitable arrangements of segmented electrodes (and pairs of ganged segmented electrodes) can be used. As an example, arrangements in which pairs of segmented electrodes are arranged helically with respect to each other. One embodiment includes a double helix with the electrodes at each longitudinal position along the two helices ganged together.

As an alternative to ganging segmented electrodes together using conductors, the segmented electrodes (or a subset of segmented electrodes) can be coupled to a multiplexer (which is preferably disposed in the lead near the electrodes) or to controllable switches (which are preferably disposed in the lead near the electrodes). The multiplexer or controllable switches can be used to electrically gang segmented electrodes together, but can also be used to change which electrodes are ganged together, if desired.

Figures 4A, 4B:
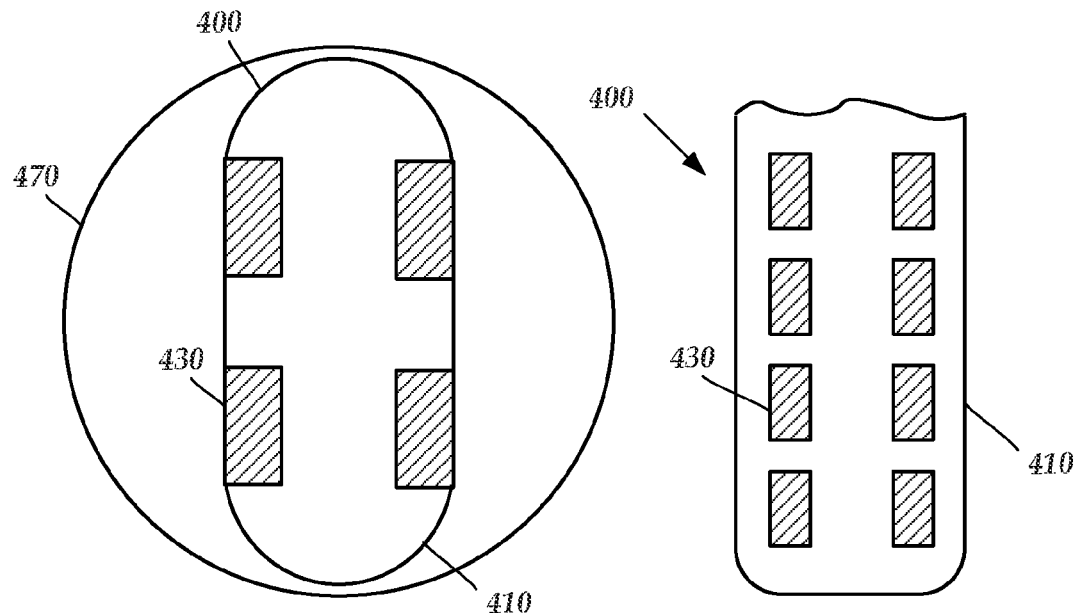
FIG. 4A is a schematic cross-sectional view of one embodiment of a lead with a non-circular cross-sectional shape that can be implanted using a percutaneous introducer, according to the invention.
FIG. 4B is a schematic top plan view of a portion of one embodiment of the lead of FIG. 4A with an example of an electrode arrangement, according to the invention.

Other lead configurations can also be used. For example, FIGS. 4A and 4B illustrate portions of a lead 400 with a lead body 410 having a non-circular cross-section and including two elongated surfaces upon which electrodes 430 are disposed. This lead 400 is sized so that it can be implanted percutaneously using an introducer 470 such as a percutaneous needle or cannula.

The lead body 410 can have any suitable non-circular cross-sectional shape including, but not limited to, oval, rectangular, square, or rectangular/square with rounded corners (as illustrated in FIG. 4), or the like. In some embodiments, the non-circular cross-sectional shape of the lead extends the entire length of the lead. In other embodiments, the non-circular cross-sectional shape of the lead only extends a portion (for example, a portion including the region near the distal end upon which the electrodes are disposed) of the length of the lead with the remainder of the lead having a circular cross-sectional shape (for example, a portion including the proximal end of the lead).

The lead body 410 has two opposing surfaces upon which electrodes 430 can be disposed. These surfaces may be flat or curved. The electrodes are coupled to terminals (not shown) on the proximal end of the lead by conductors (not shown) that extend along the length of the lead.

The electrodes can be formed using any biocompatible conductive material. Examples of suitable materials include metals, alloys, conductive polymers, conductive carbon, and the like, as well as combinations thereof. In at least some embodiments, one or more of the electrodes are formed from one or more of: platinum, platinum iridium, palladium, titanium nitride, or rhenium.

The electrodes 430 can be disposed in an array on each of the surfaces of the lead, as illustrated in FIG. 4B. The number of electrodes 430 in the array of electrodes on a particular surface of the lead may vary. For example, there can be two, three, four, five, six, seven, eight, nine, ten, eleven, twelve, thirteen, fourteen, fifteen, sixteen, or more electrodes. As will be recognized, other numbers of electrodes may also be used. The electrodes 140 can be formed in any suitable shape including, for example, round, oval, triangular, rectangular, pentagonal, hexagonal, heptagonal, octagonal, or the like. The electrodes 430 of an array can be arranged in any arrangement including arrangements with in one or more columns, one or more rows, or both rows and columns (as illustrated in FIG. 4B). The electrodes 430 in a row or column may be aligned with an adjacent row or column or may be staggered with respect to an adjacent row or column. There may be an array of electrodes 430 on two opposing sides of lead 400, as illustrated in FIG. 4A. The arrays on the two opposing sides can be the same or different.

The electrodes 430 are typically disposed in, or separated by, a non-conductive, biocompatible material of the lead body 410 including, for example, silicone, polyurethane, and the like or combinations thereof. The lead body 410 may be formed in the desired shape by any process including, for example, molding (including injection molding), casting, and the like. Electrodes and connecting wires can be disposed onto or within the lead body either prior to or subsequent to a molding or casting process.

In some embodiments, electrodes 430 on opposite sides (and, preferably, directly opposite each other) of the lead body 410 can be ganged together in a manner similar to that illustrated for the embodiments of FIGS. 3A-3D. In some embodiments, electrodes 430 on the same side of the lead body 410 (for example, electrodes in a row or column) can be ganged together.

Figure 6A:
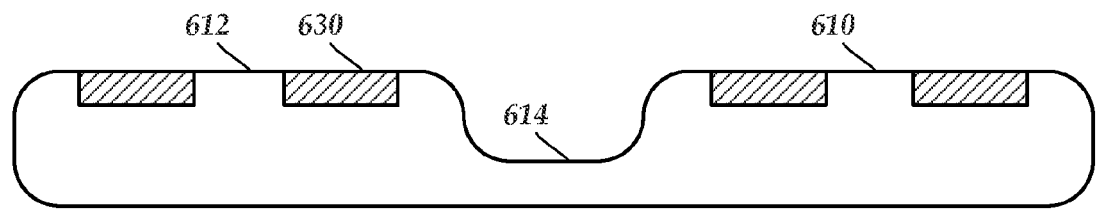
FIG. 6A is a schematic cross-sectional view of one embodiment of a lead having two main portions, each containing electrodes, separated by a bendable portion, according to the invention.
Figure 6B:
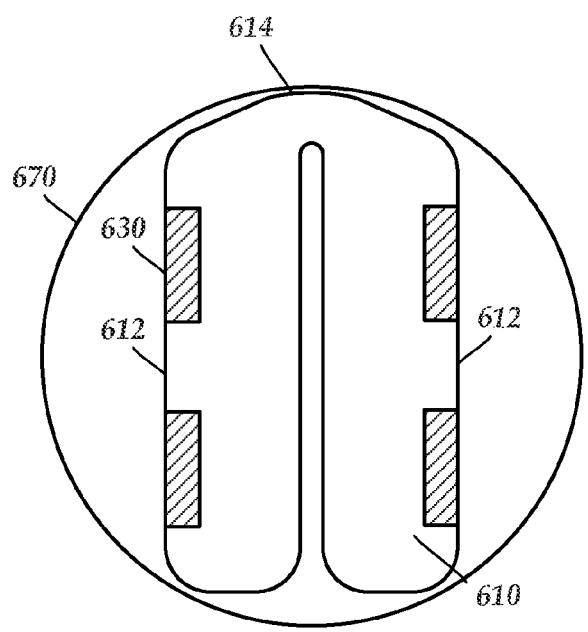
FIG. 6B is a schematic cross-sectional view of one embodiment of the lead of FIG. 6A with the bendable portion bent and the lead disposed in a percutaneous introducer, according to the invention.

A lead with a lead body having a non-circular cross-sectional shape and electrodes disposed thereon can be formed using an suitable technique including forming a lead body around electrodes disposed in two sides of a mold. In at least some instances, it may be easier or more economical to form electrodes on one side of a lead body. FIGS. 6A and 6B illustrate one method for forming a lead body 610 having a non-circular cross-sectional shape and electrodes 630 disposed on opposing sides of the lead body. As illustrated in FIG. 6A, a lead body 610 with electrodes 630 disposed on one side of the lead body is formed. For example, the electrodes 630 can be attached to conductors (not shown) which can extend along the lead to terminals or contact on a distal end of the lead. These electrodes 630 can be placed in a mold and then the lead body 610 molded around the electrodes 630 leaving a surface of each electrode exposed.

In these embodiments, the lead body 610 includes two main portions 612 divided by a bendable portion 614. The electrodes are disposed on the two main portions 612. In at least some embodiments, the bendable portion 614 has a thickness that is substantially less than a thickness of the two main portions. In some embodiments, the bendable portion 612 may include one or more hinges, one or more holes, one or more reduced-thickness portion, or any other suitable structure that facilitates bending or folding of the bendable portion.

In forming the lead with electrodes on opposing sides, the bendable portion 614 is bent so that the two main portions 612 are disposed opposite each other, as illustrated in FIG. 6B. This lead body 610 can be inserted into an introducer 670. In some embodiments, the bendable portion 614 contains material that retains the bend once bent. In other embodiments, the bendable portion 614 is resilient and may spring back to its original shape or some intermediate position. Optionally, one or more fasteners (e.g., straps, hooks, and the like), sutures disposed around the lead body, or adhesive may be provided to retain the lead body 610 in the bent shape. In other embodiments, the lead body 610 retains the bent shape once implanted due to the presence of adjacent tissue.

When implanting a lead, particularly in the brain, it can be useful to provide a recording electrode that can be used to identify the tissue that is to be stimulated. In many conventional procedures, a recording electrode lead is inserted into an introducer and the introducer is inserted into the patient. The introducer is then moved through the tissue using the recording electrode to identify which tissue is to be stimulated. Once the desired tissue is identified, the recording electrode lead is removed from the introducer and a stimulating electrode lead is inserted. This conventional procedure can take additional time for removal and insertion of multiple leads. Moreover, the introducer may inadvertently move during removal of the recording electrode lead and the insertion of the stimulating electrode lead which may result in the stimulating electrode lead being no longer aligned with the desired tissue.

Figure 5:
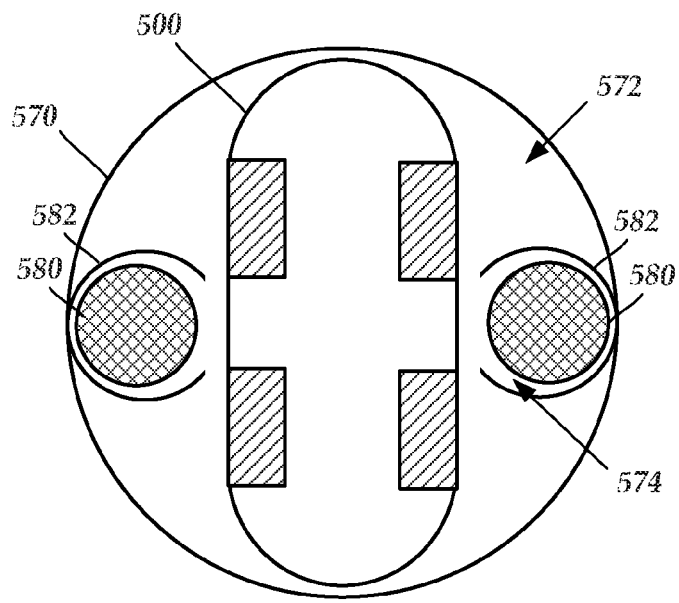
FIG. 5 is a schematic cross-sectional view of one embodiment of a lead disposed in an introducer that also contains microelectrode lumens for receiving microelectrode leads, according to the invention.

A system can be provided that addresses this issue by providing an introducer and lead that can be used simultaneously with a microelectrode lead. FIG. 5 illustrates one embodiment of such a system with an introducer 570 (e.g., a cannula or a needle) defining an introducer lumen 572 into which a stimulation lead 500 (which can correspond to the lead 400 of FIGS. 4A and 4B) can be inserted. Within the introducer lumen 572, one or more microelectrode lumens 574 are formed using one or more walls 582. FIG. 5 illustrates two microelectrode lumens, but in other embodiments only one microelectrode lumen is provided. A microelectrode lead 580 can be inserted with each microelectrode lumen 574 formed within the introducer 570. The microelectrode lead 580 includes a microelectrode at a tip of the microelectrode lead 580 which can be used as a recording electrode to identify tissue to be stimulated. The microelectrode lead 580 may be, for example, a guidewire or other suitable lead structure.

The walls 582 which form the microelectrode lumens 574 can be cylindrical or any other suitable shape. The walls 582 surround the entire lumen (e.g., have a circular cross-section) or may include openings (for example, have a C-shape in cross-section, as illustrated in FIG. 5). In some instances, a portion of the wall of the introducer may form part of the wall 582 of the microelectrode lumens 574. The walls 582 may extend the entire length of the introducer 570 or may only extend partway along the introducer, for example, partway from the distal end or the proximal end or a combination thereof.

The arrangement illustrated in FIG. 5 allows for the introducer 570 to contain both the microelectrodes lead(s) 580 and the stimulation lead 500 simultaneously. In some embodiments, both the microelectrode lead(s) 580 and stimulation lead are inserted into the introducer prior to insertion of the introducer into the patient. In other embodiments, the microelectrode lead(s) may be inserted into the introducer prior to, or after, insertion of the introducer into the patient and then the microelectrode lead(s) are used to identify the tissue to be stimulated. Later, the stimulation lead may be inserted into the introducer with the microelectrode lead(s) remaining in the introducer. The microelectrode lead(s) can be used to verify that the stimulation lead is properly positioned after it insertion into the introducer in the patient.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead, comprising:
   a lead body defining a longitudinal surface, a distal end, and a proximal end, wherein the lead body has a non-circular cross-sectional shape;
   two main portions disposed at the distal end of the lead body;
   a bendable portion disposed between the two main portions and thinner than the two main portions;
   a plurality of electrodes disposed on a surface of each of the two main portions of the lead to form at least one column of electrodes on each of the two main portions; and
   a plurality of terminals disposed along the proximal end of the lead body and electrically coupled to the plurality of electrodes,
   wherein each column of electrodes comprises at least two of the electrodes and wherein the bendable portion is configured and arranged to bend so that the two main portions are disposed opposite each other.

2. The lead of claim 1, wherein the bendable portion comprises one or more hinges or one or more holes.

3. The lead of claim 1, wherein a surface of the bendable portion is recessed relative to the surface of each of the two main portions upon which the plurality of electrodes are disposed.

4. The lead of claim 1, wherein the bendable portion is resilient and configured and arranged to spring back to its original shape after being bent.

5. The lead of claim 1 wherein the bendable portion extends parallel to each of the at least one column of electrodes.

6. A kit, comprising:
   the lead of claim 1; and
   an introducer defining a lumen configured and arranged to receive the lead only when the bendable portion is bent.

7. The kit of claim 6, wherein the introducer further comprises at least one interior wall extending into the lumen and defining at least one microelectrode lumen that is configured and arranged to receive a microelectrode lead.

8. The kit of claim 7, further comprising a microelectrode lead configured and arranged to be received within the at least one microelectrode lumen of the introducer, wherein the microelectrode lead comprises a distal end and at least one microelectrode disposed along the distal end of the microelectrode lead.

9. A method for stimulating tissue, the method comprising:
implanting the lead of claim 1, wherein the bendable portion is bent so that the two main portions are disposed opposite each other and wherein each electrode has an exposed surface through which electrical energy can be supplied to stimulate adjacent tissue when the lead is implanted;
retaining the lead in the patient with the bendable portion bent; and
stimulating adjacent tissue using at least one of the electrodes.

10. The method of claim 9, wherein implanting a lead comprises inserting at least the distal end of the lead body into an introducer defining a lumen configured and arranged to receive the lead, the introducer further comprising at least one interior wall extending into the lumen and defining at least one microelectrode lumen that is configured and arranged to receive a microelectrode lead.

11. The method of claim 10, wherein implanting a lead further comprises inserting a microelectrode lead into the at least one microelectrode lumen of the introducer.

12. The method of claim 11, wherein implanting a lead further comprises using the microelectrode lead to identify tissue for stimulation.

13. A kit for implanting a stimulation lead into a patient, the kit comprising:
a stimulation lead comprising a longitudinal surface, a distal end, and at least one electrode disposed along the longitudinal surface of the stimulation lead along the distal end of the stimulation lead, wherein a portion of the stimulation lead upon which the electrodes are disposed has a non-circular cross-sectional shape; and
an introducer defining a lumen configured and arranged to receive the stimulation lead, the introducer further comprising at least one interior wall extending into the lumen and defining at least one microelectrode lumen that is configured and arranged to receive, and hold within the at least one microelectrode lumen, a microelectrode lead.

14. The kit of claim 13, further comprising at least one microelectrode lead comprising a distal end and at least one microelectrode disposed along the distal end of the microelectrode lead, wherein the at least one microelectrode lead is configured and arranged to be received in the at least one microelectrode lumen.

15. The kit of claim 13, wherein the introducer comprises two interior walls defining two microelectrode lumens.

16. The kit of claim 15, wherein the two microelectrode lumens are disposed opposite each other within the lumen of the introducer.

17. The kit of claim 13, wherein the stimulation lead further comprises a proximal end, two main portions disposed at the distal end of the stimulation lead, a bendable portion disposed between the two main portions, and a plurality of terminals disposed along the proximal end of the stimulation lead and electrically coupled to the plurality of electrodes, wherein the bendable portion is configured and arranged to be bendable so that the two main portions are disposed opposite each other and the plurality of electrodes are disposed on a surface of each of the two main portions of the stimulation lead, wherein each electrode has an exposed surface through which electrical energy can be supplied to stimulate adjacent tissue when the stimulation lead is implanted.

18. A method for stimulating tissue using the kit of claim 13, the method comprising:
inserting at least the distal end of the stimulation lead into the introducer;
inserting a microelectrode lead into the at least one microelectrode lumen of the introducer, wherein the microelectrode lead comprises a distal end and at least one microelectrode disposed along the distal end of the microelectrode lead;
implanting the stimulation lead using the microelectrode lead to identify tissue for stimulation; and
stimulating adjacent tissue using at least one of the electrodes.

19. The method of claim 18, wherein the introducer comprises two interior walls defining two microelectrode lumens and wherein inserting a microelectrode lead comprising inserting a microelectrode lead into each of the two microelectrode lumens of the introducer.

20. The method of claim 19, wherein the two microelectrode lumens are disposed opposite each other within the lumen of the introducer.

* * * * *